United States Patent
Yamada

(10) Patent No.: US 8,546,763 B2
(45) Date of Patent: Oct. 1, 2013

(54) POSITRON COMPUTED TOMOGRAPHY DEVICE

(75) Inventor: Yoshihiro Yamada, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 385 days.

(21) Appl. No.: 12/863,615

(22) PCT Filed: Jan. 22, 2008

(86) PCT No.: PCT/JP2008/050802
§ 371 (c)(1),
(2), (4) Date: Jul. 20, 2010

(87) PCT Pub. No.: WO2009/093305
PCT Pub. Date: Jul. 30, 2009

(65) Prior Publication Data
US 2010/0284600 A1    Nov. 11, 2010

(51) Int. Cl.
*G01T 1/29*    (2006.01)
*G06T 5/30*    (2006.01)
*A61B 6/14*    (2006.01)

(52) U.S. Cl.
USPC ............ 250/363.04; 382/131; 600/431

(58) Field of Classification Search
USPC ............... 250/363.04; 382/131; 600/431
See application file for complete search history.

(56) References Cited

U.S. PATENT DOCUMENTS
5,378,893 A * 1/1995 Murray et al. ........... 250/363.03

OTHER PUBLICATIONS

Takahashi et al. (2007). "System Modeling of Small Bore DOI-PET Scanners for Fast and Accurate 3D Image Reconstruction." 2007 IEEE Nuclear Science Symposium Conference Record. p. 3478-3481.*
Takahashi, Hisashi et al., "Imaging System Models for Small Bore DOI-PET Scanners", JAMIT Annual Meeting, 2006, proceedings OP10-7.
Nakayama, Takayuki et al., "Derivation and Implementation of Ordered-Subsets Algorithms for List-Mode PET Data", 2005 IEEE Nuclear Science Symposium Conference Record, 2005, pp. 1950-1954.
Tanaka, Eiichi et al., "Subset-Dependent Relaxation in Block-Iterative Algorithms for Image Reconstruction in Emission Tomography", Physics in Medicine and Biology, 2003, vol. 48, pp. 1405-1422.
Tonami, Hiromichi et al., "Sophisticated 32×32×4-Layer DOI Detector for High Resolution PEM Scanner", 2007 IEEE Nuclear Science Symposium Conference Record, 2007, pp. 3803-3807.

* cited by examiner

*Primary Examiner* — David Porta
*Assistant Examiner* — Casey Bryant
(74) *Attorney, Agent, or Firm* — Cheng Law Group, PLLC

(57) ABSTRACT

In a positron CT device of this invention, a cross range calculation section determines a cross range of a coincidence LOR as a virtual line that connects two detectors for performing coincidence and a pixel, and a system matrix calculating section determines a system matrix by calculating elements in the system matrix within the cross range upon calculating of the system matrix. Thereafter, a reconstruction section creates a distribution image of positrons as an image based on the system matrix. Consequently, improvement in speed of image reconstruction may be realized.

3 Claims, 4 Drawing Sheets

POSITRON COMPUTED TOMOGRAPHY DEVICE

TECHNICAL FIELD

This invention relates to a positron computed tomography (CT) device to detect radiation emitted from a positron emission drug that is administered to a subject and to create a distribution image of positrons as an image.

BACKGROUND ART

A positron CT device, i.e., a PET (Positron Emission Tomography) device reconstructs an image of a subject only upon detection of positrons, i.e., gamma rays generated in annihilation of the positrons and detection of the gamma rays simultaneously with a detector (that is, only upon coincidence).

The PET device of this type doses a subject with a radiopharmaceutical, and thereafter determines accumulation of the drug in a target tissue temporally. As a result, various body functions may be determined quantitatively. Consequently, an image that the PET device obtains has functional information.

Description will be given in detail to a human body as one example of a subject. Positron radioisotope, such as $^{15}O$, $^{18}F$, and $^{11}C$, is injected inside the subject body to detect gamma rays to be generated upon binding of positrons emitted from the radioisotope to electrons. The gamma rays are detected with a row of detectors that are composed of numerous gamma-ray detectors arranged in a ring shape so as to surround a body axis as a longitudinal axis of the subject. Thereafter, a computer calculates in the same process as the conventional X-ray computed tomography to specify gamma rays in a plane, thereby creating an image of the subject.

The following process is adopted in image reconstruction. See, for example, Non-patent Literatures 1 and 2. Let a pixel formed in three-dimensional voxels within an FOV (Field of View) be denoted by $v_j$ (j=0, 1, ..., J−1), and i-th LOR (Line Of Response) by $L_i$ (i=0, 1, ..., I−1.) Here, LOR is a virtual line connecting two detectors that perform coincidence. Where the pixel is composed of three-dimensional voxels, LOR corresponds to a tube region made by connecting two detectors that detects two gamma-ray photons generated from each voxel and emitted in the opposite directions.

In reconstruction of PET images, i.e. a probability that gamma-ray photons emission from voxel $v_j$ is detected in the LOR ($L_i$), has an important function. The $a_{ij}$ is referred to as a "system matrix." As for formulization of image reconstruction, see Non-patent Literatures 1 and 2.

It is difficult to calculate $a_{ij}$ precisely. One process is used to provide sampling points inside the detectors on both ends of each $L_i$ and to make approximation of the sum of the probability $a_{ij}^{(s)}$ where the gamma-ray photons generated from $v_j$ are detected in a minute region of the detectors with the following Equation (4). See, for example, Non-patent Literature 3.

[Non-Patent Literature 1]
Nakamura T, Kudo H: Derivation and implementation of ordered-subsets algorithms for list-mode PET data, IEEE Nuclear Science Symposium Conference Record: 1950-1954, 2005

[Non-Patent Literature 2]
Tanaka E, Kudo H: Subset-dependent relaxation in block-iterative algorithms for image reconstruction in emission tomography. In: Phys Med Biol 48, 1405-1422, 2003

[Non-Patent Literature 3]
Hisashi Takahashi, Taiga Tamaya, Tetsuya Kobayashi et al.: Imaging system models for small bore DOI-PET scanners, JAMIT Annual Meeting 2006 proceedings OP10-7

[Non-Patent Literature 4]
H. Tonami, K. Kitamura, M. Satoh, T. Tsuda, and Y. Kumazawa, "Sophisticated 32×32×4-Layer DOI Detector for High Resolution PEM Scanner," IEEE Medical Imaging Conference Record, pp. 3803-3807, 2007

DISCLOSURE OF THE INVENTION

Problem to be Solved by the Invention

However, a high resolution PET device has been required strongly. For the high resolution, there needs a large number of LORs I and voxels J. In this case, calculation of an extremely large number of $a_{ij}$ is required, which results in increased time for reconstructing images. Particularly, when the pixel as mentioned above is formed of the three-dimensional voxels, a number of the LOR I or the voxel J increases, which may lead to increased time for reconstructing images remarkably.

This invention has been made regarding the state of the art noted above, and its object is to provide a positron CT device capable of realizing improvement in speed for image reconstruction.

Means for Solving the Problem

This invention is constituted as stated below to achieve the above object. A positron CT device of this invention includes detectors to detect radiation emitted from a positron emission drug that is administered to a subject and to output electric signals, a coincidence circuit to detect simultaneous observation of the radiation in two of the detectors based on the electric signals, a system matrix calculation unit to calculate a system matrix based on output from the coincidence circuit, and a reconstruction unit to create a distribution image of positrons as an image based on the system matrix, the positron CT device further including a cross range calculation unit to determine a cross range of a coincidence LOR as a virtual line that connects the two detectors for performing coincidence and a pixel, the system matrix calculating unit determining a system matrix by calculating elements in the system matrix within the cross range.

According to the positron CT device of this invention, the cross range calculation unit determines a cross range of the coincidence LOR as a virtual line that connects the two detectors for performing coincidence and the pixel. Upon calculation of a system matrix, a system matrix has been conventionally obtained by calculating elements of all data in the system matrix within a field of view, whereas, with the positron CT device of this invention, a system matrix calculating unit determines a system matrix by calculating elements in the system matrix within the cross range. Thereafter, the reconstruction unit creates a distribution image of the positrons as an image based on the system matrix. Consequently, data required prior to calculation of the system matrix are reduced from all data within the conventional field of view into that in the cross range. Thus, the cross range just need be performed initialization that is required for calculation of the system matrix, which results in increased efficiency. Moreover, access to a memory device that memorizes the cross range may be improved in efficiency by an amount of reduced data to the cross range, which also results in improved efficiency in calculation of the system matrix. As a result, improvement in speed of the image reconstruction may be realized.

In one exemplary embodiment of the positron CT device of this invention, the pixel mentioned above is formed of three-dimensional voxels, and the cross range calculating unit determines the three-dimensional cross range by making appropriation with a hexahedron that circumscribes the detectors on both ends of the LOR. For determining the three-dimensional cross range, assuming a smallest hexahedron as possible that contains the detectors on both ends of the LOR. Here, the hexahedron mentioned above that circumscribes the detectors is the smallest. The three-dimensional cross range may be determined by making appropriation assuming that the voxel crossing the hexahedron is a voxel that may cross the LOR.

Each plane that forms the hexahedron is preferably of a rectangle or a square. Setting of such hexahedron results in a rectangular or square section of the hexahedron where the LOR crosses perpendicularly. Moreover, each side of the section of the hexahedron is also parallel to a border plane of the voxel. The hexahedron also has a three-dimensional array in size of "a long side× a short side× one side of the Field of View (FOV)" of the hexahedron. Therefore, program development may be simplified on initialization required for calculation of the system matrix mentioned above.

Effect Of The Invention

According to the positron CT device of this invention, the cross range calculation unit determines the cross range of the coincidence LOR as a virtual line that connects the two detectors for performing coincidence and the pixel, and the system matrix calculating unit determines the system matrix by calculating elements in the system matrix within the cross range mentioned above upon calculating of the system matrix. Consequently, improvement in speed of image reconstruction may be realized.

DESCRIPTION OF REFERENCES

3 . . . gamma-ray detector
10 . . . cross range calculation section
11 . . . system matrix calculation section
12 . . . reconstruction section
$L_i$ . . . i-th LOR
A' . . . retention array (showing cross range)
$a_{ij}$ . . . probability (element in system matrix)
$v_j$ . . . voxel
HEX . . . hexahedron
M . . . subject

[Embodiment]

Figure 1:
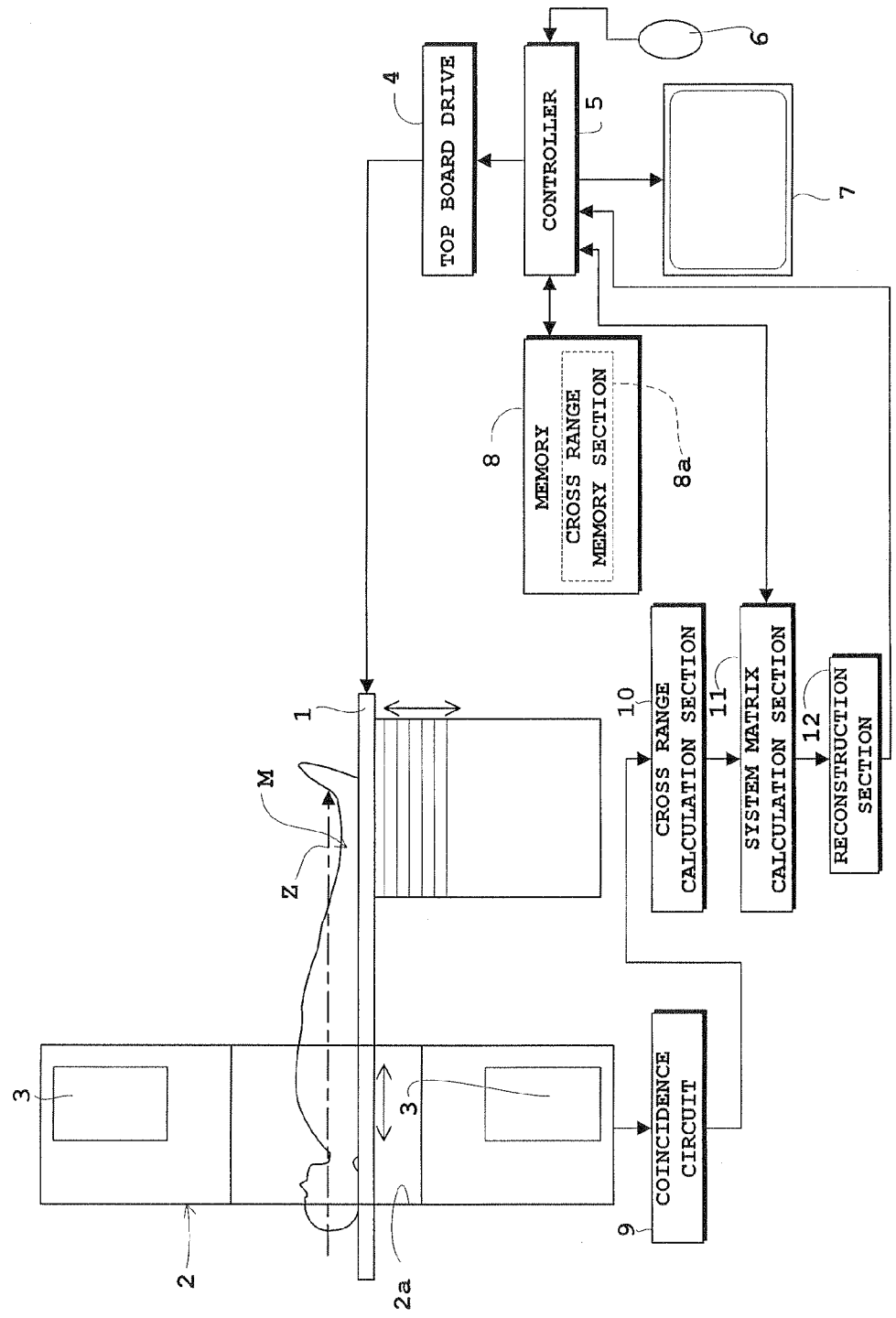
FIG. 1 is a side view and block diagram of a PET (Positron Emission Tomography) device according to one embodiment.
Figure 2:
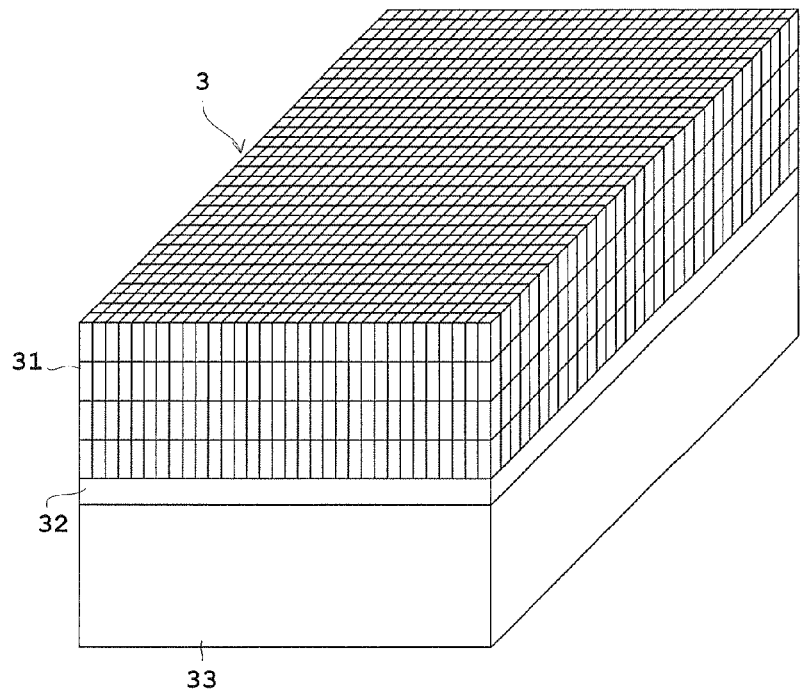
FIG. 2 is a schematic perspective view of a gamma-ray detector.

One embodiment of this invention will be described in detail hereinafter with reference to the drawings. FIG. 1 is a side view and block diagram of a PET (Positron Emission Tomography) device according to this embodiment. FIG. 2 is a schematic perspective view of a gamma-ray detector.

As shown in FIG. 1, the PET device of this embodiment includes a top board 1 to support a subject M. The top board 1 moves upward and downward, and moves horizontally along a body axis Z of the subject M. With this configuration, the subject M supported on the top board 1 is passed through an opening 2a of a gantry 2, mentioned later, and scanned from the head to the abdomen and legs, in turn, to obtain an image of the subject M. Here, each area to be scanned or a scanning sequence thereof is not particularly limited.

Besides the top board 1, the PET device of this embodiment includes the gantry 2 with the opening 2a and gamma-ray detectors 3. The gamma-ray detectors 3 are arranged in a ring shape so as to surround the body axis Z of the subject M, and embedded in the gantry 2. The gamma-ray detectors 3 correspond to the detectors in this invention.

Moreover, the PET device of this embodiment further includes a top board drive 4, a controller 5, an input section 6, an output section 7, a memory 8, a coincidence circuit 9, a cross range calculation section 10, a system matrix calculation section 11, and a reconstruction section 12. The top board drive 6 is a mechanism that drives the top board 1 so as to move in a manner as mentioned above. The top board drive 6 is formed of a motor, not shown, and the like. The cross range calculation section 10 corresponds to the cross range calculation unit in this invention. The system matrix calculation section 11 corresponds to the system matrix calculation unit in this invention. The reconstruction section 12 corresponds to the reconstruction unit in this invention.

The controller 5 controls each section en bloc that forms the PET device according to this embodiment. The controller 5 is formed of a central processing unit (CPU) and the like.

The input section 6 transmits data or commands that an operator inputs to the controller 5. The input section 6 is formed of a pointing device represented by such as a mouse, keyboard, joystick, trackball, and touch panel. The output section 7 is formed of a display screen represented by a monitor, and a printer.

The memory 8 is formed of a storage medium represented by such as a ROM (Read-only Memory), and RAM (Random-Access Memory.) In this embodiment, data on coincidence such as a count value (count) at which the coincidence circuit 9 performs coincidence counting, a pair of detectors composed of two gamma-ray detectors 3 that performs coincidence counting, and an LOR, data for the cross range obtained by the cross range calculation section 10, a system matrix that the system matrix calculation section 11 calculates, or images processed in the reconstruction section 12 is written and stored into the RAM and read out from the RAM, as required. Specifically, in this embodiment, the memory 8 has in its memory area a cross range memory section 8a capable of storing data for the cross range that is obtained by the cross range calculation section 10. The data for the cross range is written and stored into the cross range memory section 8a, and read out from the cross range memory section 8a upon calculation of the system matrix by the system matrix calculation section 11. Programs for imaging including various types of nuclear medicine diagnoses are stored in advance in the ROM. The controller 5 executes a program to perform each nuclear medicine diagnosis in accordance with the program.

The cross range calculation section 10, system matrix calculation section 11, and reconstruction section 12 may be realized by execution with the controller 5 of a program stored in the ROM as a storage medium represented by the memory section 8 mentioned above or a command that the pointing device representing the input section 6 inputs.

A scintillator block 31 (see FIG. 2) of the gamma-ray detector 3 converts gamma rays generated from the subject M with the radiopharmaceutical administered thereto into light. A photo multiplier tube (PMT: Photo Multiplier Tube) 33 (see FIG. 2) of the gamma-ray detector 3 multiplies the converted light to convert into electric signals. The electric signals are transmitted to the coincidence circuit 9 as image information (a pixel value, i.e., a counting value at which the gamma-ray detector 3 performs coincidence counting.)

Particularly, upon administration of the radiopharmaceutical to the subject M, a positron of positron emission type RI annihilates to generate two gamma rays. The coincidence circuit 9 confirms the position of the scintillator block 31 (see FIG. 2), and incidence timing of gamma rays. Only when gamma rays enter simultaneously into the two scintillator blocks 31 on both sides of the subject M, image information transmitted is interpreted to be appropriate data. When gamma rays enter into only one scintillator block 31, the coincidence circuit 10 rejects image information that is transmitted. That is, the coincidence circuit 9 detects simultaneous observation of the gamma rays in the two gamma-ray detectors 3 based on the electric signals mentioned above.

The image information transmitted to the coincidence circuit 9 is sent to the cross range calculation section 10, system matrix calculation section 11, and reconstruction section 12. The reconstruction section 12 performs reconstruction in accordance with the system matrix calculated in the system matrix calculation section 11 to obtain an image of the subject M. Specifically, the reconstruction section 12 creates the distribution image of positrons as an image based on the system matrix. The image is sent to the output section 7 via the controller 5. As mentioned above, nuclear medicine diagnosis is to be performed based on the image obtained in the reconstruction section 12. Detailed functions of the cross range calculation section 10 and system matrix calculation section 11 will be described later.

As shown in FIG. 2, the gamma-ray detector 3 includes a scintillator block 31, a light guide 32 optically connected to the scintillator block 31, and a photo multiplier tube (hereinafter, simply abbreviated as "PMT") 33 optically connected to the light guide 32. Each scintillator element that forms the scintillator block 31 converts gamma rays into light by emitting light upon incidence of the gamma rays. The scintillator element detects gamma rays through this conversion. The light emitted in the scintillator element sufficiently scatters in the scintillator block 31, and enters into the PMT 33 via the light guide 32. The PMT 33 multiplies the light converted in the scintillator block 31 for conversion into electric signals. The electric signals are transmitted to the coincidence circuit 9 (see FIG. 1) as image information (pixel value), as mentioned above.

Figure 3:
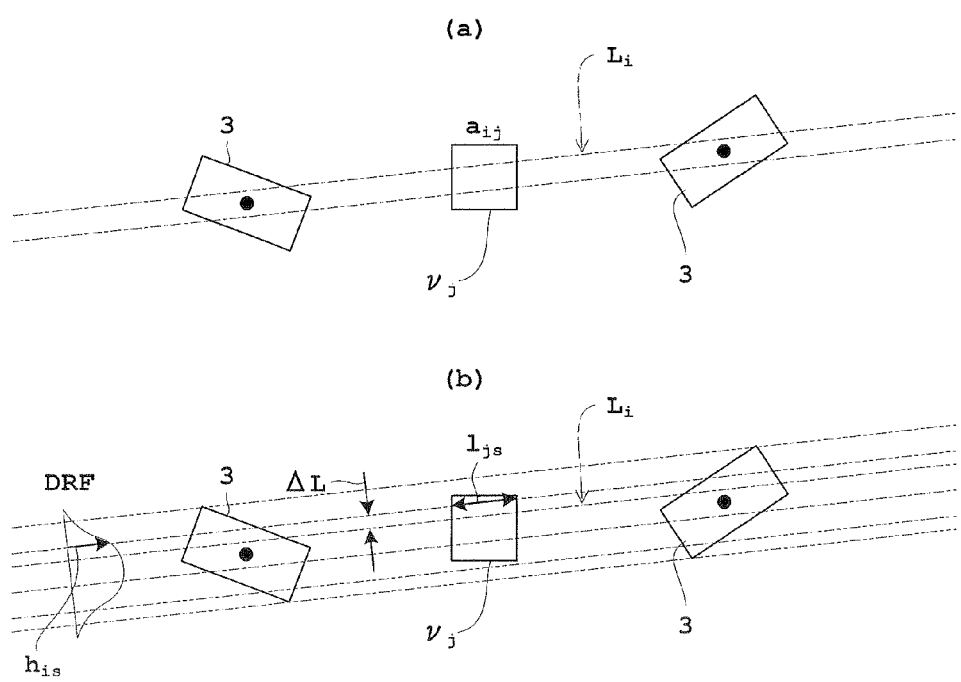
FIGS. 3(a) and 3(b) are schematic views each showing coincidence in the gamma-ray detector used for explanation of absorption probability to a minute region.
Figure 4:
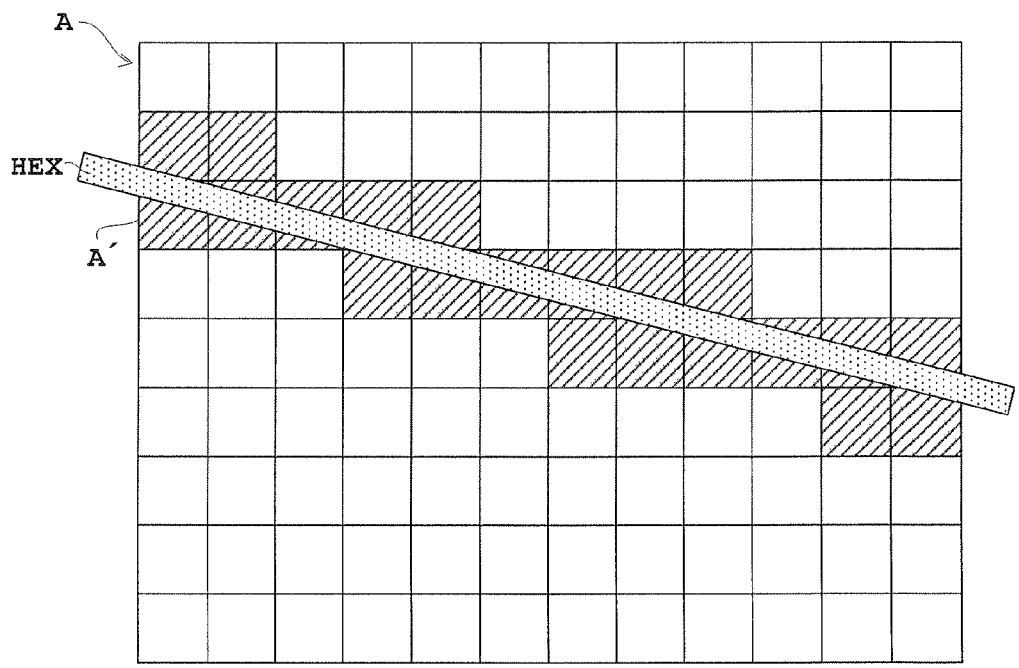
FIG. 4 is a schematic view used for explanation of voxels that may cross an LOR and a retention array.
Figure 5:
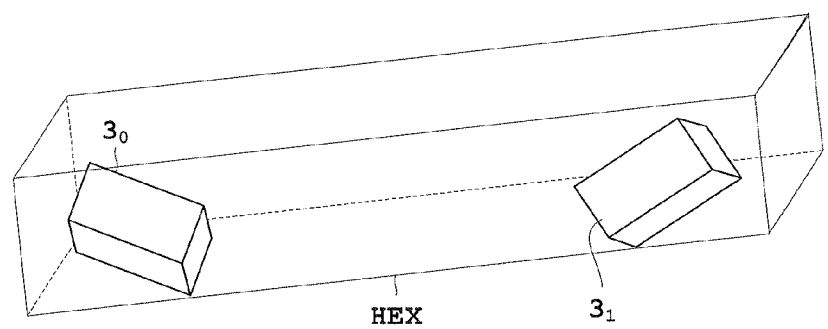
FIG. 5 is a schematic view of the hexahedron circumscribing to the gamma-ray detector.
Figure 6:
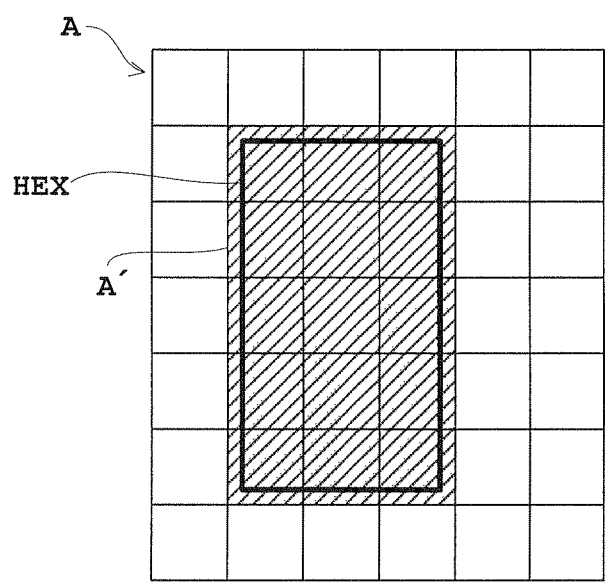
FIG. 6 is a schematic cross sectional view of the circumscribing hexahedron and voxels.

Next, detailed functions of the cross range calculation section 10 and system matrix calculation section 11 will be described with reference to FIGS. 3 to 6. FIG. 3 is a schematic view showing coincidence in a gamma-ray detector used for explanation of absorption probability to a minute region. FIG. 4 is a schematic view used for explanation of voxels that may cross an LOR and a retention array. FIG. 5 is a schematic view of a hexahedron circumscribing to the gamma-ray detector. FIG. 6 is a schematic cross sectional view of the circumscribing hexahedron and voxels. In FIGS. 3 and 5, only shown is a scintillator block 31 as the gamma-ray detector 3, and a light guide 32 and a PMT 33 are not shown.

Following Equations (1) to (4) will be described with reference to the above Non-patent Literature 3. As shown in FIG. 3(a), assume that a gamma ray photon emission from the voxel $v_j$ is detected in the i-th LOR ($L_i$) at a probability of $a_{ij}$. FIG. 3(b) is a picture in which S sub-LORs (shown in dash-dotted lines in FIG. 3(b)) are drawn at an interval $\Delta L$ with respect to a tubular $L_i$ as a target (shown in two-dot chain lines in FIG. 3.) Here, the minute region to be divided by the S sub-LORs including the target $L_i$ has also a number of S. Although the sub-LORs are shown in parallel in FIG. 3(b), the sub-LORs always need not be parallel. Moreover, the sub-LORs need not be at regular intervals.

A probability that gamma rays emitted from a position r within a field of view lead to i-th projection data is referred to as "Detector Response Function (DRF)" (shown by "DRF" in FIG. 3(b)), and denoted by $h_i(r)$. Let linear attenuation coefficient of a scintillator element be denoted as $\mu$, a path length of gamma rays within the scintillator element A be denoted as $D_{iA}$, a path length within the scintillator block 31 (see FIG. 2) prior to incidence on the scintillator element A be denoted as $D'_{iA}$, a path length of gamma rays within an observation element B be denoted as $D_{iB}$, and a path length within the scintillator block 31 (see FIG. 2) prior to incidence on the observation element B be denoted as $D'_{iB}$. Here, DRF is expressed as following Equation (1).

[Equation 1]

$$h_i(\vec{r}) = \frac{1}{2\pi}\int_0^{2\pi} \{1 - \exp[-\mu \cdot D_{Ai}(\Omega, \vec{r})]\} \cdot \{1 - \exp[-\mu \cdot D_{Bi}(\Omega, \vec{r})]\} \cdot \{\exp[-\mu \cdot D'_{Ai}(\Omega, \vec{r})]\} \cdot \{\exp[-\mu \cdot D'_{Bi}(\Omega, \vec{r})]\} d\Omega \quad (1)$$

As shown in FIG. 3(b), let $h_i(r)$ given by the above Equation (1) be denoted as $h_{is}$ in a certain minute region s and a length of each sub-LOR including the target $L_i$ that crosses the voxel $v_j$ be denoted as $l_{js}$. Here, an element of the system matrix (i.e., probability $a_{ij}$) is expressed as following Equation (2) in which the length $l_{js}$ mentioned above is weighted by DRF ($h_{is}$) and added.

[Equation 2]

$$a_{ij} = \sum_{s=0}^{S-1} h_{is} \cdot l_{js} \quad (2)$$

The absorption probability $a_{ij}^{(s)}$ at which gamma rays are to be detected in the minute region s of the detector is expressed as the following Equation (3) from the product of $h_{is}$ and $l_{js}$ ($h_{is} \cdot l_{js}$) in the above Equation (2).

[Equation 3]

$$a_{ij}^{(s)} = h_{is} \cdot l_{js} \quad (3)$$

Therefore, when summarizing the above Equations (2) and (3), we express $a_{ij}$ following Equation (4) by a sum of absorption probability $a_{ij}^{(s)}$.

[Equation 4]

$$a_{ij} = \sum_{s=0}^{S-1} a_{ij}^{(s)} \quad (4)$$

Conventionally, $a_{ij}$ as an element of the system matrix may be determined by preparing an array A (FIG. 4) for each $L_i$ that is equal in number to the voxel and adding $a_{ij}^{(s)}$ with the above Equation (4). In fact, however, the LOR has a thin tube shape. Consequently, most of the voxels $v_j$ fail to cross the LOR ($L_i$), which leads to $a_{ij}$ of "0" that corresponds to such voxels $v_j$ not crossing. Here, in this embodiment, the cross range calculation section 10 (see FIG. 1) determines $a_{ij}$ by listing the voxels $v_j$ that may cross the LOR ($L_i$) in advance, preparing an array A' (see FIG. 4) that retains only $a_{ij}$ corresponding to the voxels and adding $a_{ij}^{(s)}$ with the above Equation (4).

Specifically, as shown in FIG. 4, in order to determine the cross range of the LOR ($L_i$) and the voxels $v_j$, the cross range calculation section 10 (see FIG. 1) determines the retention array A' showing the cross range in the array A equal in number to the voxels $v_j$ within the field of view showing the entire image. The voxels $v_j$ that may cross the LOR ($L_i$) are depicted with backward slashes in FIG. 4.

To obtain the cross range mentioned above, the detectors $3_0$ and $3_1$ on both ends of the LOR are circumscribed by a hexahedron HEX. For determination of the three-dimensional cross range, suppose a smallest hexahedron HEX as possible that contains the detectors $3_0$ and $3_1$ on both ends of LOR. Here, the hexahedron mentioned above that circumscribes the detectors $3_0$ and $3_1$ is the smallest. The three-dimensional cross range may be determined by making appropriation assuming that the voxels $v_j$ crossing the hexahedron HEX are voxels $v_j$ that may cross the LOR ($L_i$). That is, now returning to FIG. 4 for description, an aggregate of the voxels $v_j$ in a minimum region including the hexahedron HEX corresponds to the cross range shown by the backward slashes in FIG. 4.

The hexahedron HEX mentioned above is preferably set to have each plane of a rectangle or square that forms the hexahedron. Setting of such hexahedron HEX results in a rectangular or square section of the hexahedron where LOR ($L_i$) crosses perpendicularly, as shown in FIG. 6. Moreover, each side of the section of the hexahedron (shown by a bold frame in FIG. 6) is also parallel to a border plane of the voxel. Here, each section of the cross range is also shown by backward slashes in FIG. 6. The hexahedron also has a three-dimensional array in size of "a long side× a short side× one side of the Field of View (FOV)" (where the section is square, "(one side of the section)²× one side of the Field of View (FOV)") of the hexahedron. Therefore, program development may be simplified on initialization that is required for calculation of the system matrix mentioned above.

The retention array A' determined in such a manner is written and stored into the cross range memory section 8a (see FIG. 1) as data for the cross range, and read out from the cross range memory section 8a upon calculation of the system matrix by the system matrix calculation section 11 (see FIG. 1.) As mentioned above, the system matrix calculation section 11 may calculate $a_{ij}$ as an element of the system matrix by preparing data for the cross range (retention array A') that is read out from the cross range memory section 8a and adding $a_{ij}^{(s)}$ with the above Equation (4).

The reconstruction section 12 performs reconstruction based on the system matrix calculated in the system matrix calculation section 11. Description will be given of the reconstruction based on the system matrix with reference to the above Non-patent Literature 1. Here, description will be made under application of a list-mode DRAMA method (Dynamic Row-Action Maximum Likelihood Algorithm.) Let the pixel value to be reconstructed be denoted as $x_j$, and T LORs to be performed coincidence with the gamma-ray detector 3 be denoted as i(t) (t=0, 1, . . . T−1). When the LOR to which coincidence has been performed is divided into M subsets, and each of the subsets is denoted as Sq (q=0, 1, . . . , M−1), $x_j$ is expressed by following Equations (5) to (10) with $a_{ij}$ as an element of the system matrix.

[Equation 5]

$$x_j^{(k,0)} = x_j^{(k)} \quad (5)$$

$$x_j^{(k,q+1)} = x_j^{(k,q)} + \lambda_k(q) \cdot \frac{x_j^{(k,q)}}{C_j} \cdot \sum_{i \in S_q} a_{i(t)j} \cdot \left( \frac{1}{\langle a^i, x^{(k,q)} \rangle} - p_{qj} \right) \quad (6)$$

where $$C_j = \max_q \sum_{i \in S_q} a_{ij} \quad (7)$$

$$x_j^{(k+1)} = x_j^{(k,M-1)} \quad (8)$$

$$\langle a^i, x \rangle = \sum_{j=0}^{J-1} a_{ij} \cdot x_j \quad (9)$$

$$0 < \lambda_k(q) \leq 1 \quad (10)$$

where, $P_{qj}$ is a positive number that satisfies Equation:

$$\sum_i a_{ij} = \sum_q \sum_{t \in S_q} a_{i(t)j} \cdot p_{qj},$$

and is referred to as Blocking Factor.

$\lambda_k(q)$ in the above Equations (6) and (10) is a relaxation parameter. $C_j$ in the above Equations (6) and (7) is a normalization matrix. $P_{qj}$ is called "Blocking Factor." The above Equation (6) implies calculating of $x_j^{(k,q+1)}$ using $a_{ij}$ calculated in the system matrix calculation section 11 (see FIG. 1) and $x_j^{(k,q)}$ previously calculated. Consequently, substitution of $a_{ij}$ and $x_j^{(k,0)}$ in the above Equation (6) is performed repeatedly, and $x_j^{(k,1)}$, . . . , $x_j^{(k,M-1)}$ is determined sequentially. In the above Equation (8), $x_j^{(k,M-1)}$ finally determined is substituted, thereby being advanced to $x_j^{(k+1)}$. Subsequently, $x_j^{(k+1)}$ is substituted in the above Equation (5) to be $x_j^{(k+1,0)}$. Similarly, substitution of $a_{ij}$ and $x_j^{(k+1,0)}$ in the above Equation (6) is performed repeatedly, and $x_j^{(k+1,1)}$, . . . , $x_j^{(k+1,M-1)}$ is determined sequentially. Here, k is a superscript for $x_j$, and indicates a frequency of successive approximation in a successive approximation equation as shown in the above Equation (6). Here, $x_j^{(0)}$ as an initial value is assumed $x_j^{(0)} > 0$.

In summary, $x_j^{(0)}$ as an initial value is determined, and the determined $x_j^{(0)}$ is substituted in the above Equation (5) to obtain $x_j^{(0,0)}$. Subsequently, substitution of $a_{ij}$ and $x_j^{(0,0)}$ in the above Equation (6) is performed repeatedly, to sequentially obtain $x_j^{(0,1)}$, . . . , $x_j^{(0,M-1)}$. In the above Equation (8), $x_j^{(0,M-1)}$ finally obtained is substituted, thereby being advanced to $x_j^{(1)}$. Hereinafter, $x_j$ is to be advanced in order in a similar manner ($x_j^{(0)}, x_j^{(1)}, \ldots, x_j^{(k)}$). The number of k is not particularly limited, but may be set appropriately. The reconstruction section 12 (see FIG. 1) performs reconstruction by arranging $x_j$ finally obtained in such a manner in order for every voxel $v_j$ corresponding thereto, thereby obtaining an image of the subject M.

A method for the reconstruction based on the system matrix is not limited to the DRAMA method mentioned above. A static RAMLA method (Row-Action Maximum Likelihood Algorithm), ML-EM method (Maximum Likelihood Expectation Maximization), or OSEM method (Ordered Subset ML-EM) may be adopted. The reconstructing is preferably performed using the successive approximation by a successive approximation equation such as Equation (6).

According to the PET device of this invention having the above configurations, the cross range calculation section 10 determines the cross range of the coincidence LOR as a virtual line that connects the two detectors for performing coincidence and the pixel. Upon calculation of a system matrix, a system matrix is conventionally obtained by calculating elements of all data in the system matrix within a field of view, whereas, with the PET device of this invention, a system matrix calculating section 10 determines a system matrix by calculating an element $a_{ij}$ in the system matrix within the cross range that are stored in the cross range memory 8a using the above Equation (4). Thereafter, the reconstruction section 12 creates a distribution image of the positrons as an image based on the system matrix. Consequently, data required prior to calculation of the system matrix is reduced from all data (array A) within the conventional field of view into that in the cross range (retention array A'). Thus, the cross range just need be performed initialization that is required for calculation of the system matrix, which results in increased efficiency. Moreover, access to the cross range memory 8a that memorizes the cross range may be improved in efficiency by an amount of reduced data to the cross range, which may also result in improved efficiency in calculation of the system matrix. As a result, improvement in speed of image reconstruction may be realized.

This invention is not limited to the foregoing embodiment, but may be modified as follows.

(1) In the embodiment mentioned above, the positron CT device (PET device) is individually adopted. This embodiment is also applicable to a PET-CT device in combination of a PET device and CT device.

(2) In the embodiment mentioned above, the pixel is formed of the three-dimensional voxels, and the three-dimensional cross range is determined by making appropriation with the hexahedron that circumscribes the detectors on both ends of the LOR. This embodiment is also applicable to a pixel formed of two-dimensional pixels. In this case, a two-dimensional cross range may be determined by making appropriation with a parallelogram or rectangle that circumscribes the detectors on both ends of the LOR.

The invention claimed is:

1. A positron CT device comprising detectors to detect radiation emitted from a positron emission drug that is administered to a subject and to output electric signals, a coincidence circuit to detect simultaneous observation of the radiation in two of the detectors based on the electric signals, a system matrix calculation unit to calculate a system matrix based on output from the coincidence circuit, and a reconstruction unit to create a distribution image of positrons as an image based on the system matrix, the positron CT device further comprising a cross range calculation unit to determine a cross range of a coincidence LOR as a virtual line that connects the two detectors for performing coincidence and a pixel, and the system matrix calculating unit determining a system matrix by calculating only elements in the system matrix within the cross range determined by the cross range calculation unit, the elements corresponding to the cross range.

2. The positron CT device according to claim 1, wherein the pixel is formed of three-dimensional voxels, and the cross range calculating unit determines the three-dimensional cross range by making appropriation with a hexahedron that circumscribes the detectors on both ends of the LOR.

3. The positron CT device according to claim 2 wherein each plane that forms the hexahedron is of a rectangle or a square.

* * * * *